Figure 1:
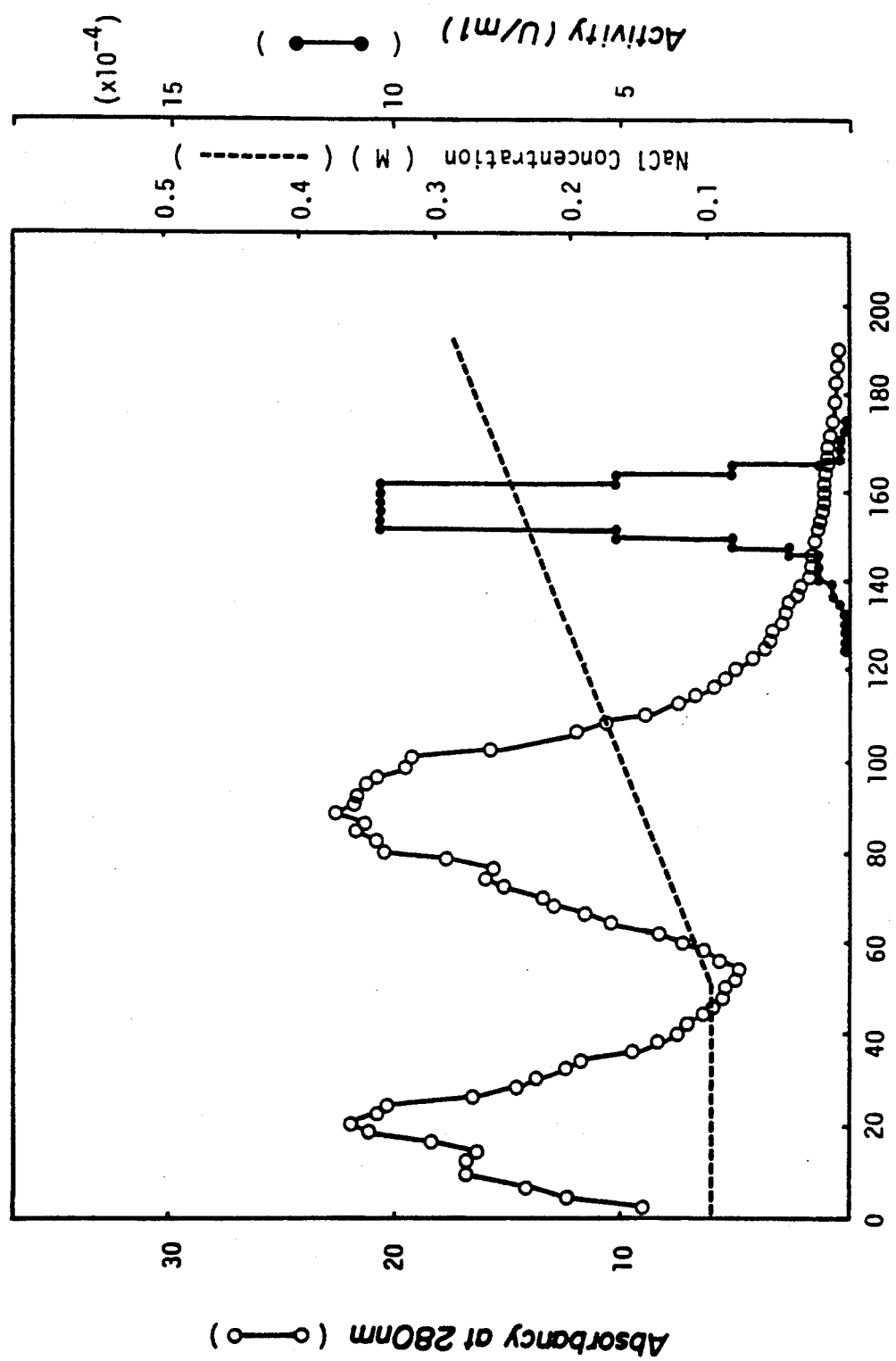

United States Patent [19]

Haranaka et al.

[11] Patent Number: 5,023,320

[45] Date of Patent: Jun. 11, 1991

[54] PROCESS FOR THE PURIFICATION OF PHYSIOLOGICALLY ACTIVE SUBSTANCE HAVING ANTITUMOR ACTIVITY

[75] Inventors: Katsuyuki Haranaka, Kokubunji, Japan; Lloyd J. Old, New York, N.Y.; Elizabeth C. Richards, Westport; Barbara Williamson, Old Greenwich, both of Conn.

[73] Assignee: Sloan-Kettering Institute For Cancer Research, New York, N.Y.

[21] Appl. No.: 219,093

[22] Filed: Jul. 14, 1988

Related U.S. Application Data

[63] Continuation of Ser. No. 360,972, Mar. 23, 1982, abandoned.

[51] Int. Cl.$^5$ .................. C07K 15/04; C07K 3/28
[52] U.S. Cl. ................... 530/350; 530/413; 530/416; 530/417; 530/351; 530/820; 530/822; 530/824; 530/825; 530/826
[58] Field of Search ............... 530/413, 416, 417, 350, 530/351, 820, 822, 824, 825, 826; 514/21

[56] References Cited

PUBLICATIONS

Brit. J. of Cancer, (1978), 38, 302–309, Matthews et al.
Chem. Abstracts, vol. 92 (1980, 108513h, Matthews.
Brit. J. of Cancer (1980), 42, 416–422, Matthews et al.
Proc. Natl-Acad. Sci. U.S.A., (1975), 72, No. 9, 3666–3670, Carswell et al.
J. Immunology, (1980), 125, No. 4, 1671–1677, Ruff et al.
Brit. J. Cancer (1981), 44, 418–424 (Matthews).

*Primary Examiner*—Howard E. Schain
*Attorney, Agent, or Firm*—John P. White

[57] ABSTRACT

A process is provided for the purification of a proteinaceous physiologically active substance having antitumor activity, which is induced by administering to a rabbit at least one substance having a capacity for stimulating reticuloendothelial system and then injecting endotroxin from a Gram-negative bacterium into the rabbit. The process comprises contacting a crude solution of said proteinaceous physiologically active substance with a basic anion exchanger to have said physiologically active substance adsorbed on the anion exchanger, eluting the adsorbed physiologically active substance, and subjecting the eluate containing said physiologically active substance to gel filtration with a gel suitable for separation of a substance with a molecular weight in the range of 30,000 to 70,000. The purified preparation of said physiologically active substance thus obtained may be used as an antitumore agent for the treatment of malignant tumors. Said physiologically active substance is isolated by subjecting the purified preparation successively to affinity chromatography on immobilized Cibarcron Blue F3G-A, gel filtration, affinity chromatography on immobilized concanavalin A, preparative electrophoresis on polyacrylamide gel and gel filtration.

12 Claims, 2 Drawing Sheets

PROCESS FOR THE PURIFICATION OF PHYSIOLOGICALLY ACTIVE SUBSTANCE HAVING ANTITUMOR ACTIVITY

This is a continuation application of U.S. Ser. No. 360,972, filed Mar. 23, 1982, the contents of which are hereby incorporated by reference into the present disclosure, now abandoned.

This invention relates to a process for purifying a proteinaceous physiologically active substance having antitumor activity.

There have been a number of reports on the existence of substances having physiological activities such as tumor cell-killing ability, the typical examples of which are briefly reviewed in the following:

Currie et al. discovered that a factor which inhibits the proliferation of various tumor cells was induced by administration of endotoxin to peritoneal exudate cells from a normal rat [J. Exp. Med., Vol. 142, pp. 1600–1605 (1975)], and thereafter further investigation was done on said factor to find that the principle of the factor is arginase as reported in Nature (London), Vol. 273, pp. 758–759 (1978).

Reed et al. also discovered a proteinaceous substance with molecular weight of 45,000 having an ability to kill cultured tumor cells such as L cells from cultured cells or cultured mononuclear supernatant of normal rat and human by applying endotoxin treatment, but the principle of said substance has not yet been isolated and identified [J. Immunol., Vol. 115, pp. 395–404 (1975)].

Carswell et al. discovered that the serum from CD-1 Swiss mouse infected with bacillus Calmette-Guérin (BCG), and after two weeks, followed by intravenous injection of endotoxin has cytotoxic activity against cultured L cells and also a phenomenon that it induces hemorrhagic necrosis of transplanted BALB/c sarcoma Meth A in the (BALB/c×C57BL/6)F$_1$ mouse, and they gave the name of TNF (Tumor Necrosis Factor) to the active substance in the serum [Proc. Nat. Acad. Sci. USA, Vol. 72 (No. 9), pp. 3666–3670 (1975)]. Further, they conducted partial purification of TNF from said serum and consequently obtained TNF fractions purified 20- to 30-fold over the serum, reporting that the active substance is a glycoprotein having a molecular weight of about 150,000 which migrates with α-globulins in cellulose acetate electrophoresis [Proc. Nat. Acad. Sci. USA, Vol. 73 (No. 2), pp. 381–385 (1976)].

Männel et al. examined the properties of Cytotoxic Factor by the use of the mouse serum obtained by the method of Carswell et al. as mentioned above to find that upon gel filtration the eluted fractions with cytotoxic activity were varied depending on the salt concentration in the buffer and that the molecular weight of Cytotoxic Factor was 55,000 to 60,000 in a buffer with a high salt concentration, while it was 125,000 to 150,000 through aggregation in a buffer with a low salt concentration or serum [Infect. Immun., Vol. 28 (No. 1), pp. 204–211 (1980)]. They reported that the isoelectric point (pI value) of this factor was 4.8. But, the activity of this factor was not evaluated in an animal (for example, evaluation using transplanted Meth A sarcoma in mouse) and therefore the presence of its activity in vivo cannot be ascertained. It is consequently impossible to judge whether the factor is identical with TNF of Carswell et al. Further, they mentioned almost nothing about its purification and isolation, although some properties of it were examined based on cytotoxic activity against L cells.

Matthews et al. induced TNF in a rabbit, examined the properties of the rabbit TNF from the serum and reported that the rabbit TNF had a molecular weight in the range of from 40,000 to 50,000 as measured by gel filtration using Sephadex G-200 [Br. J. Cancer, Vol. 38, pp. 302–309 (1978)]. However, they also reported that the molecular weight was 67,000 on gradient polyacrylamide gel electrophoresis or 39,000 on gel filtration with Ultrogel AcA 44 [Br. J. Cancer, Vol. 42, pp. 416–422 (1980)]. But, since they used no isolated and purified sample, it is not certain whether the TNF is a single substance or not.

Ruff et al. reported that the rabbit TNF was purified 2,000-fold over the serum and that the molecular weight of the rabbit TNF was estimated to be 68,000 by SDS-polyacrylamide gel electrophoresis, 55,000 by gel filtration using Sephacryl-200 and 52,000 by glycerol gradient centrifugation [J. Immunol., Vol. 125 (No. 4), pp. 1671–1677 (1980)].

Kull et al. obtained three kinds of tumor cell cytotoxin fractions from the mouse serum obtained by the method of Carswell et al. as mentioned above and conducted tests using transplanted Meth A sarcoma in mouse, reporting that the fraction with molecular weight of 160,000 induced tumor necrosis, while the fractions with molecular weights of 225,000 and 50,000 induced no tumor necrosis [J. Immunol., Vol. 126 (No. 4), pp. 1279–1283 (1981)].

As described above, in spite of a number of reports on the existence of various physiologically active factors, they are not obtained in most cases in amount sufficient for extensive examination of their properties. In addition, since no isolation is accomplished, it is not certain under the present situation whether they are known substances or novel substances.

Using various kinds of mammals, the present inventor has investigated the production and purification of a physiologically active substance having antitumor activity which is induced by administering to a mammal a substance having a capacity for stimulating the reticuloendothelial system and injecting endotoxin into the mammal, and found that a rabbit is most suitable for the practical application of the physiologically active substance as a medicine.

An object of the present invention is to provide a practical and highly valuable process for purifying a physiologically active substance having antitumor activity which is induced by administering to a rabbit a substance having a capacity for stimulating the reticuloendothelial system and injecting endotoxin into the rabbit.

Another object of the present invention is to provide a novel physiologically active substance having antitumor activity which is induced by administering to a rabbit a substance having a capacity for stimulating reticuloendothelial system and injecting endotoxin into the rabbit.

The present invention relates to a process for purifying a proteinaceous physiologically active substance having antitumor activity, which is induced by administering to a rabbit at least one substance having a capacity for stimulating the reticuloendothelial system and then injecting endotoxin from a Gram-negative bacterium into the rabbit, which comprises contacting a crude solution of said proteinaceous physiologically active substance with a basic anion exchanger to have said physiologically active substance adsorbed on the anion exchanger, eluting the adsorbed physiologically active substance, and subjecting the eluate containing said physiologically active substance to gel filtration with a gel suitable for separation of a substance with a molecular weight in the range of 30,000 to 70,000.

In order to induce the physiologically active substance according to the present invention (hereinafter referred to as the present physiologically active substance), at least one substance having a capacity for stimulating the reticuloendothelial system is first injected intravenously or intraperitoneally into a rabbit according to the method of Carswell et al. [Proc. Nat. Acad. Sci. USA, Vol. 72 (No. 9), pp. 3666-3670 (1975)]. As the substances having a capacity for stimulating the reticuloendothelial system, there are generally used Gram-positive bacteria, protozoas or yeasts, which are administered to the rabbit in the form of either living microorganisms, dead microorganisms (e.g. after heat treatment or formalin treatment) or microorganism cell extracts. Examples of the Gram-positive bacteria include Propionibacteria such as *Propionibacterium acnes* (*Corynebacterium parvum*) or *Propionibacterium granulosum* (*Corynebacterium granulosum*), Mycobacteria such as bacillus Calmette-Guérin (BCG) or *Mycobacterium smegmatis*, and Nocardias such as *Nocardia erythropolis* or *Nocardia gardneri*. As a protozoa, for example, Plasmodium or Toxoplasma is employable. As a yeast, Zymosan extracted from *Saccharomyces cerevisiae* or others is generally used. There may also be employable synthetic high molecular compounds such as pyran copolymer. Seven to 14 days after administration, endotoxin from a Gram-negative bacterium, for example, a lipopolysaccharide derived from *Escherichia coli, Pseudomonas aeruginosa*, or *Salmonella typhosa* is injected intravenously into said rabbit. Then, 1.5 to 2 hours after the injection, body fluids (e.g. ascites, lymph, etc.) and/or serum or plasma of said rabbit are taken or internal organs such as liver, spleen, etc. are homogenized and extracted with physiological saline solution. These body fluids, serum, plasma and/or extract of internal organs may be employed as crude solutions of the present physiologically active substance, but generally serum or plasma is employed.

Evaluation of the physiological activity of the present physiologically active substance is conducted according to the following methods.

(a) Evaluation Using L Cell

This is conducted according to the method of Carswell et al. [Proc. Nat. Acad. Sci. USA, Vol. 72 (No. 9), pp. 3666-3670 (1975)]. As a culture vessel, there is employed a plate produced by Lymbro Chemical Co., Inc. (U.S.A.) and L cells (S) are cultured in Eagle's minimum essential medium (MEM medium) containing nonessential amino acids and 10% heat-inactivated fetal calf serum, together with 100 units/ml of penicillin and 100 $\mu$g/ml of streptomycin. Equal volumes of an L cell suspension ($1 \times 10^5$ cells) and a serially diluted sample are mixed and incubated at 37° C. for 48 hours in air containing 5% carbon dioxide. The activity is determined by plotting the dilution versus the number of viable L cells on a graph and calculating from the dilution corresponding to 50% cytotoxicity, the ability to kill 50% of the L cells. The physiological activity necessary for killing 50% of L cells is defined as 1 unit.

(b) Evaluation Using Transplanted Meth A Sarcoma in Mouse

According to the method of Carswell et al. (the same literature as cited above), $2 \times 10^5$ BALB/c sarcoma Meth A cells are transplanted intradermally at the armpit of a (BALB/c$\times$C57BL/6)F$_1$ mouse and, 7 days later, mice with tumors of 7-8 mm in diameter, good vascularization and no spontaneous central necrosis are selected for evaluation. A sample (0.5 ml) diluted with physiological saline solution is injected through the tail vein. The activity of the sample is evaluated after 24 hours according to the following criterion.

(−): no change
(+): slight hemorrhagic necrosis
(++): moderate hemorrhagic necrosis (central necrosis extending over approximately 50% of the tumor surface)
(+++): marked hemorrhagic necrosis (massive necrosis leaving a small viable rim along the tumor periphery)

In the following, the purification process of this invention is described in detail.

Prior to the first step of contacting with a basic anion exchanger, a crude solution of the present physiologically active substance may be dialyzed against a buffer solution to be used at the time of contacting with an anion exchanger or it may be diluted with a buffer solution having a low salt concentration.

The contacting of a crude solution of the present physiologically active substance with a basic anion exchanger can be conducted by either column method or batch method. This step is carried out by contacting the crude solution with a basic anion exchanger using a buffer solution of pH 6.0 to 9.0 and a salt concentration of 0.2M or lower to have the present physiologically active substance adsorbed on the anion exchanger, subsequently washing said anion exchanger with the same buffer solution to remove the unadsorbed proteins and thereafter eluting the present physiologically active substance using a buffer solution of a higher salt concentration (Purification step 1).

Typical examples of basic anion exchangers used include anion exchangers containing diethylaminoethyl groups such as DEAE-Sephadex A-50, DEAE-Sepharose CL-6B, DEAE-Sephacel (all produced by Pharmacia Fine Chemicals AB, Sweden) and AIEC DE 52 (produced by Whatman Ltd., England), anion exchangers containing aminoethyl groups such as Servacel AE (produced by Serva Entwicklungslabor, West Germany), and anion exchangers containing quaternized aminoethyl groups such as QAE-Sephadex A-50 (produced by Pharmacia) and Cellex QAE (produced by Bio-Rad Laboratories, U.S.A.). The buffer solutions used include a dilute Tris-hydrochloric acid buffer, a dilute phosphate buffer and the like. Sodium chloride or potassium chloride is preferably added to adjust the salt concentration of the buffer solution. The content of protein in the eluate is determined by the optical density at 280 nm. The concentration of the present physiologically active substance is measured as the cytotoxic activity against L cells as described above.

Although the above step can be carried out with a single contact with the anion exchanger, it is sometimes preferable in the case of the column method to employ re-chromatography.

The eluate containing the present physiologically active substance obtained in the preceding step is concentrated by a conventional method such as ultrafiltration or lyophilization. The thus obtained concentrate is subjected to gel filtration using a gel suitable for separation of a substance with a molecular weight of 30,000 to 70,000 (Purification step 2). As an eluent, there is employed a buffer solution having a pH generally of 6.0 to 9.0. The salt concentration is not critical, but is preferably 0.15 to 2.0M. The gels for gel filtration include Sephadex G-75, 100, 150 or 200 (produced by Pharmacia), Sephacryl S-200 or 300 (produced by Pharmacia), Bio-Gel P-30, 60, 100, 150 or 200 (produced by Bio-Rad), CPG-10 (350 Å, 240 Å, 170 Å or 120 Å) (produced by Electro-Nucleonics, Inc., U.S.A.) and the like. Examples of the buffer solution and the salt are the same as those described above in the step of contacting with an anion exchanger.

The fractions containing the present physiologically active substance are pooled and concentrated by a conventional method such as ultrafiltration or lyophilization. The dialysis of the concentrate of the present physiologically active substance against a physiological saline solution affords a solution of said substance purified about 5,000- to 10,000-fold over the serum or plasma. The overall activity recovery of the two steps according to the evaluation using L cell is about 65 to 98%.

The thus prepared purified solution of the present physiologically active substance is adjusted to appropriate pH and salt concentration by dialysis or gel filtration, sterilized by filtration, and if necessary, heated, and lyophilized to give a purified preparation of the present physiologically active substance.

The purified preparation in an amount of about 3,000 units was found to exhibit (++) activity in the evaluation using Meth A sarcoma as described above. The purified preparation of the present physiologically active substance was also found to exhibit cytotoxic activity against various cultured human cancer cell lines. The percent cytotoxicity at 48 hours after administration of 800 units of the purified preparation is shown in Table 1.

TABLE 1

| Cancer cell lines | Percent cytotoxicity | Medium* |
| --- | --- | --- |
| PC 10 | 69.1 | a |
| KATO-III | 67.9 | b |
| MK-7 | 65.8 | a |
| Rca | 66.8 | c |
| W-2 | 75.9 | a |
| GOTO | 61.3 | b |
| SEKI | 70.0 | b |
| Kym-1 | 51.9 | d |
| MRK-1-nu | 75.1 | d |

*a: 80% RPMI 1640 + 20% FCS
b: 40% RPMI 1640 + 40% MEM + 20% FCS
c: 80% MEM + 20% FCS
d: 80% DM160 + 20% FCS

On the other hand, the purified preparation of the present physiologically active substance was found to exhibit no cytotoxic activity against normal cells such as cultured fibroblasts of human and mouse even in a dose of $2 \times 10^6$ units.

Further, in the tests in which the purified preparation of the present physiologically active substance was administered to a BALB/c mouse with transplanted Colon 26 adenocarcinoma and a A/Jax mouse with transplanted Neuro-2a neuroblastoma, there were seen significant growth inhibition and regression of the tumors as compared with a Control Group (Group to which physiological saline solution was administered). The grown tumors regressed or disappeared without causing hemorrhagic necrosis in some animals.

The purified preparation of the present physiologically active substance has an extremely excellent antitumor activity, which is lower in species specificity, and it can be used as an antitumor agent for the treatment of malignant tumors in a mammal including humans.

The purified preparation of the present physiologically active substance is generally administered parenterally or topically in the form of an aqueous solution to which an isotonic agent such as sodium chloride or/and a buffering agent such as phosphate may be optionally added. The clinical dosage of the purified preparation of the present physiologically active substance, which may vary depending on the route of administration, and the condition as well as the body weight of the patient, is generally about $10^4$ to $10^8$ units per one administration for a human adult. The purified preparation of the present physiologically active substance may also be used in combination with other antitumor agents such as cyclophosphamide, mitomycin C, adriamycin and bleomycin.

The purified preparation of the present physiologically active substance obtained as described above can further be subjected to the steps shown below, whereby the present physiologically active substance can be isolated:

(3) Affinity chromatography on immobilized Cibacron Blue F3G-A;
(4) Gel filtration;
(5) Affinity chromatography on immobilized concanavalin A;
(6) Preparative electrophoresis on polyacrylamide gel; and
(7) Gel filtration.

Each of these steps is described in detail below.

Purification Step 3

The concentrate of the present physiologically active substance obtained in step 2 is subjected to affinity chromatography on immobilized Cibacron Blue F3G-A (dye produced by Ciba-Geigy Corp.). Immobilization of Cibacron Blue F3G-A on a support may be performed according to a known method as described by Böhme et al. in J. Chromatogr., Vol. 69, pp. 209–214 (1972), or alternatively, commercially available adsorbent [e.g. Blue Sepharose CL-6B (produced by Pharmacia), Affi-Gel Blue (produced by Bio-Rad)] may be used. After the concentrate of the present physiologically active substance is dialyzed against a dilute buffer solution of pH 7.0 to 8.0 (e.g. phosphate buffer or Tris-hydrochloric acid buffer), it is applied to the above immobilized Cibacron Blue F3G-A. By this operation, contaminating proteins such as albumin are adsorbed on immobilized Cibacron Blue F3G-A and the present physiologically active substance is eluted in unadsorbed fractions. The activity recovery at this step is about 70 to 95% with about 3-fold increase in purity. The overall activity recovery through the purification steps 1 to 3 is about 56 to 93% with the purity being increased about $1.5 \times 10^4$- to $3 \times 10^4$-fold.

Purification Step 4

The unadsorbed fractions in step 3 are concentrated and the concentrate is subjected to gel filtration under the same conditions as in step 2. As the support for gel filtration, there may be employed Sephadex G-75, 100, 150 or 200 (produced by Pharmacia), Bio-Gel P-30, 60, 100, 150 or 200 (produced by Bio-Rad). The active fractions are pooled, concentrated and dialyzed against a dilute phosphate buffer or Tris-hydrochloric acid buffer of pH 7.0 to 8.0. The activity recovery at this step is about 70 to 95% with about 3- to 4-fold increase in purity.

The overall activity recovery through purification steps 1 to 4 is about 47 to 88% with the purity being increased about $4.5 \times 10^4$- to $9 \times 10^4$-fold.

Purification Step 5

The purified solution obtained in step 4 is subsequently subjected to affinity chromatography using immobilized concanavalin A.

Concanavalin A can be immobilized by a known method or alternatively a commercially available immobilized concanavalin A (produced by Sigma Chemical Co., U.S.A.) or Con A-Sepharose CL-6B (produced by Pharmacia) may be used. The purified solution obtained in step 4 is concentrated and applied to immobilized concanavalin A using a dilute buffer solution of pH 7.0 to 8.0 as used in the same step, and then, after washing the column with the same buffer solution, elution is performed with the same buffer solution containing 0.1M or more of α-methyl-d-mannoside. The present physiologically active substance is concentrated in unadsorbed fractions. The activity recovery at this step is about 60 to 80% with about 2- to 4-fold increase in purity. The overall activity recovery through the purification steps 1 to 5 is about 33 to 70% with the purity being increased about $9.0 \times 10^4$- to $3.6 \times 10^5$-fold.

Purification Step 6

The solution containing the present physiologically active substance obtained in step 5 is concentrated and subjected to polyacrylamide-slab electrophoresis. The concentrate of the present physiologically active substance is applied on an 8% polyacrylamide gel prepared by the use of slab electrophoresis apparatus Model 221 ($280 \times 140 \times 1.5$ mm) produced by Bio-Rad Laboratories. Electrophoresis is performed while maintaining the current at about 70 to 100 mA. After migration, the gel is cut into strips each of 3 mm width and each gel strip is extracted with a dilute buffer solution of pH 7.0 to 8.0 containing 1.0M sodium chloride, and the active fractions are pooled and concentrated. The activity recovery at this step is about 5 to 10% with about 15- to 20-fold increase in purity. The overall activity recovery through purification steps 1 to 6 is about 2.5 to 7.0% with the purity being increased about $1.4 \times 10^6$- to $5.4 \times 10^6$-fold.

Purification Step 7

In the gel filtration of this step, the same buffer, salt and gel as employed in step 2 can be used. But the length and the diameter of the column to be used in this step are longer and smaller, respectively, than those of the column employed in step 2. The active fractions are pooled, concentrated, dialyzed, sterilized by filtration and, if necessary, lyophilized to provide the novel physiologically active substance of the present invention. The activity recovery at this step is about 50 to 80% with about 1.5 to 2.0-fold increase in purity. The overall activity recovery through the purification steps 1 to 7 is about 1.6 to 5.6% with the purity being increased about $2.8 \times 10^6$- to $8.1 \times 10^6$-fold.

The characteristics of the present physiologically active substance thus prepared were measured to obtain the results shown below:

(a) Molecular weight
$39,000 \pm 5,000$ (by SDS-polyacrylamide gel electrophoresis and gel filtration)

(b) Isoelectric point
pH $3.9 \pm 0.3$ (c) Cellulose acetate electrophoresis mobility
$10^{-4}$ to $10^{-6}$ cm$^2$/V·sec (d) Specific activity by evaluation using L cells
at least $0.5 \times 10^9$ units/mg-protein Further, $2 \times 10^5$ Meth A sarcoma cells were transplanted intradermally at the armpit of (BALB/c$\times$C57BL/6)F$_1$ mice and permitted to proliferate sufficiently to form solid tumors and thereafter the present physiologically active substance was administered intravenously (at a dose corresponding to 0.1 to 1 micrograms of protein per mouse), whereby activities of (+) or higher were exhibited.

Among the above characteristics, (a) to (c) were measured according to the following methods:

(a) Determination of Molecular Weight (i) According to the method of Segrest et al.[Methods in Enzymology Vol. 28-B, pp. 54–63 (1972)] 5 μg of a sample is applied on SDS (sodium dodecyl sulfate)-polyacrylamide gel and electrophoresis is carried out in SDS/Tris-glycine buffer (pH 8.3). Calibration of the molecular weight is conducted by the use of a standard molecular weight kit (produced by Pharmacia).

(ii) Using a column ($0.9 \times 120$ cm) of Sephadex G-200 (produced by Pharmacia), gel filtration is performed using a buffer solution of 0.7M sodium chloride/0.02M Tris-hydrochloric acid buffer (pH 7.8), and calibration of the molecular weight is conducted by the use of standard proteins (ribonuclease A, chymotrypsinogen A, ovalbumin, aldolase, produced by Pharmacia).

(b) Determination of Isoelectric Point

The isoelectric point is determined using the apparatus for isoelectric electrophoresis, Ampholine (pH range 2.5 to 4.5) and 36% Ultrodex (all produced by LKB Productor AB, Sweden). The formation of a pH gradient is effected at 340 V and 23 mA for 5 to 7 hours and thereafter a sample is applied on the slab. Migration is conducted up to 660 V and 120 mA for 5 to 7 hours. Strips having a width of 1 mm are prepared and extracted with physiological saline solution and cytotoxic activity against L cells is measured.

(c) Mobility in Electrophoresis

Using Separax-S (produced by Fuji Photo Film Co., Ltd., Japan) as cellulose acetate membrane, electrophoresis is performed at pH 8.6 and ionic strength of 0.06 to 0.07. After completion of migration, strips having a width of 1 mm are prepared, extracted with physiological saline solution and evaluated for cytotoxic activity against L cells to determine the mobility.

The present physiologically active substance was tested for its cytotoxic activity against various cultured human cancer cell lines. Table 2 shows the results in terms of the corresponding protein amount necessary for 50% cytotoxicity after 48 hours.

TABLE 2

| Cancer cell lines | Amount necessary for 50% cytotoxicity (pg) | Medium* |
|---|---|---|
| PC 10 | $5 \times 10^2$ | a |
| KATO-III | $9 \times 10^2$ | b |
| MK-7 | $9 \times 10^2$ | a |

TABLE 2-continued

| Cancer cell lines | Amount necessary for 50% cytotoxicity (pg) | Medium* |
|---|---|---|
| Rca | $6 \times 10^2$ | c |
| W-2 | $8 \times 10^2$ | a |
| GOTO | $1 \times 10^3$ | b |
| SEKI | $3 \times 10^2$ | b |
| Kym-1 | $1 \times 10^3$ | d |
| MRK-1-nu | $7 \times 10^2$ | d |

*a: 80% RPMI 1640 + 20% FCS
b: 40% RPMI 1640 + 40% MEM + 20% FCS
c: 80% MEM + 20% FCS
d: 80% DM160 + 20% FCS

The present invention is further illustrated in detail by referring to the following Examples, by which the present invention is not limited.

EXAMPLE 1

Female rabbits, weighing 2.5 to 3 kg, were injected with 50 mg of formalin-killed *Propionibacterium acnes* (*Corynebacterium parvum*; Wellcome Research Laboratories, England) through the ear vein. Eight days later, 100 μg of endotoxin (lipopolysaccharide from Escherichia coli 026:B6, produced by Difco Laboratories, U.S.A.) was injected again through the ear vein and 2 hours later whole blood was collected from the heart. The collected blood was centrifuged at 5,000 rpm for 30 minutes to remove blood cells and insoluble solids. From 20 rabbits, 1,200 ml of serum having an activity of 12,800 units/ml was obtained.

The serum was diluted with 600 ml of 0.02M Tris-hydrochloric acid buffer (pH 7.8) and applied slowly to a column (6×36 cm) of DEAE-Sepharose CL-6B (Pharmacia) equilibrated with 0.02M Tris-hydrochloric acid buffer (pH 7.8) containing 0.1M sodium chloride. Then, after washing the column with 1,000 ml of equilibrating buffer (0.02M Tris-hydrochloric acid buffer, pH 7.8, containing 0.1M sodium chloride), elution was carried out with the NaCl-linear gradient formed by a gradienter, using 1.5 liters of 0.02M Tris-hydrochloric acid buffer (pH 7.8) containing 0.1M sodium chloride and 1.5 liters of 0.02M Tris-hydrochloric acid buffer (pH 7.8) containing 0.3M sodium chloride. The flow rate was 60 ml/hour and fractions each of 18 ml were collected. The active fractions were pooled and concentrated. The activity recovery at this step was 92% with 150-fold increase in purity.

Then, the concentrate was dialyzed against 0.005M phosphate buffer (pH 7.4) containing 0.15M sodium chloride overnight and gel-filtered. A column (5×80 cm) of Sephacryl S-200 (Pharmacia) was sufficiently equilibrated with the same buffer, and the concentrate was applied to the column and elution conducted with the same buffer. The flow rate was 60 ml/hour and fractions each of 10 ml were collected. The active fractions obtained immediately after the albumin fraction were concentrated by ultrafiltration to obtain a purified preparation of the present physiologically active substance. At this step, the activity recovery was 92% with 52-fold increase in purity. The overall activity recovery through all the steps was 85% with the purity being increased 7,800-fold. The purified preparation of the present physiologically active substance was found to have a specific activity of about $1.4 \times 10^6$ units/mg-protein.

Figure 2:
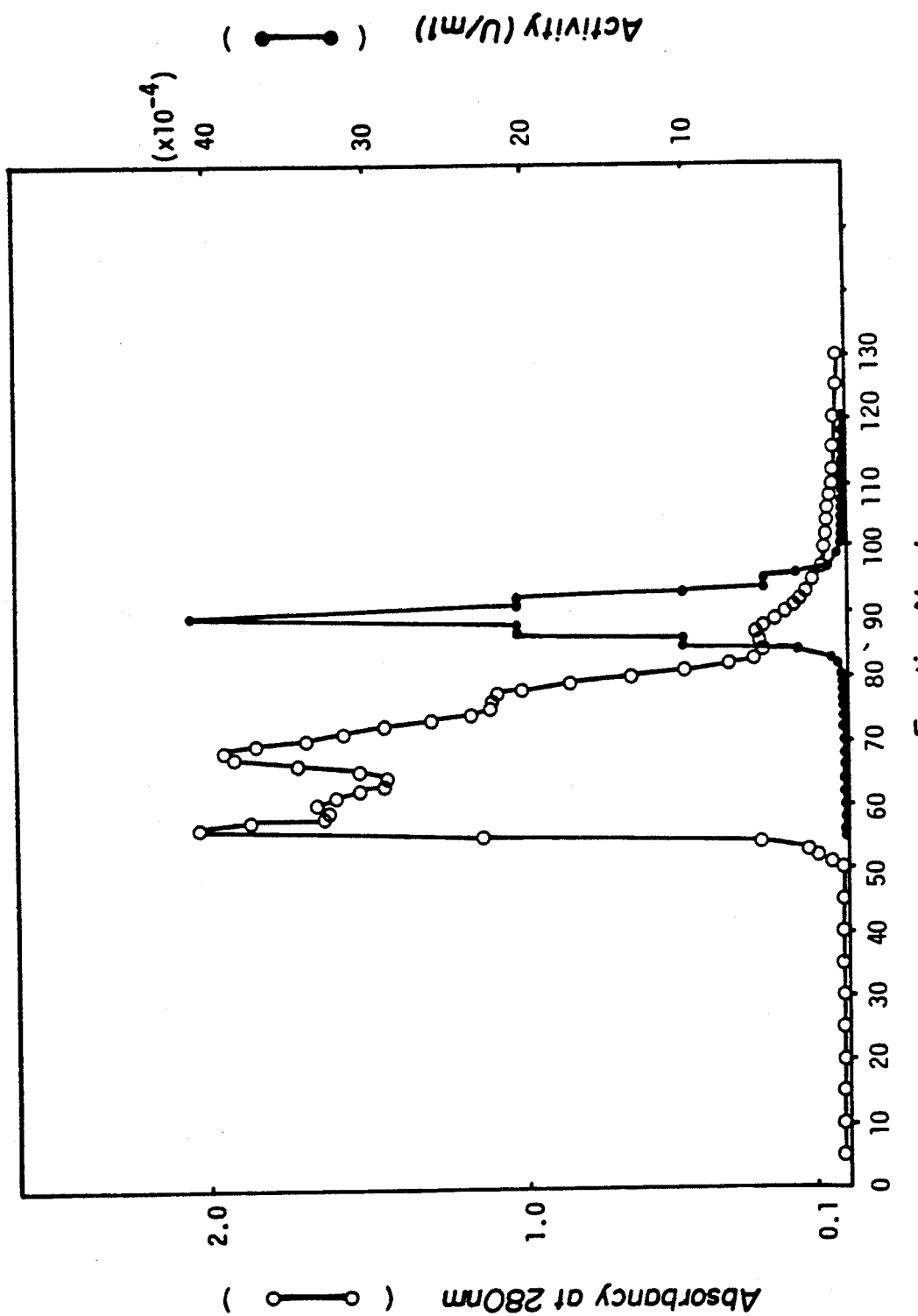

FIGS. 1 and 2 show the patterns of chromatography on DEAE-Sepharose CL-6B column at the first step and gel filtration on Sephacryl S-200 column at the second step, respectively.

EXAMPLE 2

After 2,200 ml of a rabbit serum containing the present physiologically active substance was diluted with 1,200 ml of 0.02M Tris-hydrochloric acid buffer (pH 7.2), the resulting solution was slowly applied to a column (8×26 cm) of DEAE-Sepharose CL-6B equilibrated with 0.02M Tris-hydrochloric acid buffer (pH 7.2) containing 0.1M sodium chloride. Then, the column was washed with 1,000 ml of 0.02M Tris-hydrochloric acid buffer (pH 7.2) containing 0.13M sodium chloride, and elution was carried out with the NaCl-linear gradient formed by a gradienter, using 2.0 liters of 0.02M Tris-hydrochloric acid buffer (pH 7.2) containing 0.15M sodium chloride and 2.0 liters of 0.02M Tris-hydrochloric acid buffer (pH 7.2) containing 0.3M sodium chloride. The flow rate was 90 ml/hour and fractions each of 18 ml were collected.

The pooled active fractions were dialyzed against 0.02M Tris-hydrochloric acid buffer (pH 7.2) containing 0.1M sodium chloride, and subjected to rechromatography on a column (2.5×30 cm) of DEAE-Sepharose CL-6B equilibrated with the same buffer. The present physiologically active substance adsorbed was eluted with the NaCl-linear gradient formed by a gradienter, using 350 ml of equilibrating buffer and 350 ml of 0.02M Tris-hydrochloric acid buffer (pH 7.2) containing 0.3M sodium chloride. The flow rate was 25 ml/hour and fractions each of 7 ml were collected. The active fractions were pooled and concentrated.

As the next step, the concentrate was applied to a column of Sephacryl S-200 equilibrated with 0.01M Tris-hydrochloric acid buffer (pH 7.8) containing 1.0M sodium chloride and elution was performed with the same buffer. These were collected and lyophilized to obtain a purified preparation of the present physiologically active substance having a purity of 10,000-fold higher than the serum. The activity recovery through all the steps was 80%.

EXAMPLE 3

The purified concentrate obtained in Example 1 was dialyzed against 0.02M phosphate buffer (pH 7.1) overnight and applied to a column (0.7×10 cm) of Blue Sepharose CL-6B equilibrated with the same buffer. The column was washed thoroughly with the same buffer and the adsorbed substances were eluted with 50 ml of 0.02M phosphate buffer (pH 7.1) containing 1.5M sodium chloride. The flow rate was 2.5 ml/hour and fractions each of 3 ml were collected. No activity was detected in adsorbed fractions, but all activities were recovered in unadsorbed fractions. The active fractions were pooled and lyophilized. At this step, the activity recovery was 95% with 3-fold increase in purity. The overall values through all the steps were 81% for activity recovery and $2.3 \times 10^4$-fold for purity increase.

As the next step, the lyophilized product was dissolved in 1 ml of 0.02M Tris-hydrochloric acid buffer (pH 7.8) containing 0.7M sodium chloride and applied to a column (2.6×95 cm) of Sephadex G-75 (Pharmacia) equilibrated with the same buffer. The flow rate was 20 ml/hour and fractions each of 10 ml were collected. The active fractions were pooled and concentrated. At this step, the activity recovery was 95% with 3-fold increase in purity. The overall values through all the steps were 77% for activity recovery and $6.9 \times 10^4$-fold for purity.

The concentrate was subsequently dialyzed against 0.02M phosphate buffer (pH 7.2) containing 4M magnesium chloride and applied to a column (0.3 × 10 cm) of Concanavalin A-Sepharose CL-6B (Pharmacia), equilibrated with the same buffer, at a flow rate of 2.5 ml/hour. After the column was washed thoroughly with the same buffer, elution was performed with the phosphate buffer containing 0.1M α-methyl-d-mannoside. The activity was recovered in the unadsorbed fractions and no activity was detected in the adsorbed fractions. The unadsorbed fractions were concentrated and dialyzed against the phosphate buffer containing 0.15M sodium chloride. At this step, the activity recovery was 70% with two-fold increase in purity. The overall activity recovery was 54% with the purity increase being $1.4 \times 10^5$-fold.

The dialyzed solution was then applied on 8% polyacrylamide gel prepared by means of Bio-Rad slab electrophoresis apparatus Model 221 (280 × 140 × 1.5 mm) and electrophoresis was carried out at a constant current of 80 mA. After electrophoresis, the gel was cut into strips each of 3 mm width, each strip was extracted with 0.05M Tris-hydrochloric acid buffer (pH 7.8) containing 1.0M sodium chloride for 24 hours, and the active fractions were pooled and concentrated. At this step, the activity recovery was 8% with 15-fold increase in purity. The overall activity recovery was 4.3% with the purity being $2.1 \times 10^6$-fold.

Several lots of the present physiologically active substance purified up to this step were pooled and applied to a slim column (0.9 × 120 cm) of Sephadex G-200 equilibrated with 0.05M Tris-hydrochloric acid buffer (pH 7.8) containing 0.5M sodium chloride. The flow rate was 3.5 ml/hour and fractions each of 0.3 ml were collected. The active fractions were pooled, concentrated and dialyzed against physiological saline solution to obtain a solution of the present physiologically active substance. At this step, the activity recovery was 70% with 1.5-fold increase in purity. The overall activity recovery through all the seven steps was 3.0% with the purity increase being $3.2 \times 10^6$-fold. The present physiologically active substance was found to have a specific activity of about $0.57 \times 10^9$ units/mg-protein.

What is claimed is:

1. A process for purifying a proteinaceous physiologically active substance having antitumor activity, which is induced by administering to a rabbit at least one substance having a capacity for stimulating the reticuloendothelial system selected from the group consisting of Gram-positive bacteria, protozoas, yeasts, or synthetic high molecular weight compounds, and then injecting endotoxin from a Gram-negative bacterium into the rabbit, which comprises (1) contacting a crude solution of said proteinaceous physiologically active substance with a basic anion exchanger, using a buffer solution of pH 6.0 to 9.0 and salt concentration of not more than 0.2M, under conditions such that said physiologically active substance is adsorbed on the anion exchanger, (2) eluting the adsorbed physiologically active substance from the anion exchanger with a buffer solution of a salt concentration higher than 0.2M so that an eluate is produced, and (3) subjecting the eluate containing said physiologically active substance to gel filtration with a gel suitable for separation of a substance with a molecular weight in the range of 30,000 to 70,000 and an eluent comprising a buffer solution of pH 6.0 to 9.0, so that the substance is purified about 5,000- to 10,000-fold compared to the unpurified proteinaceous physiologically active substance.

2. The process according to claim 1 wherein the salt concentration of the eluent on gel filtration in step (3) is 0.15-2.0M.

3. A purified, proteinaceous physiologically active substance having antitumor activity which is induced by administering to a rabbit at least one substance having a capacity for stimulating the reticuloendothelial system selected from the group consisting of Gram-positive bacteria, protozoas, yeasts, or synthetic high molecular weight compounds, and then injecting endotoxin from a Gram-negative bacterium into the rabbit, said substance having the following characteristic properties:

(a) molecular weight by gel filtration and PAGE: 39,000 ± 5,000;

(b) isoelectric point: pH 3.9 ± 0.3;

(c) mobility in cellulose acetate electrophoresis (pH 8.6): $10^{-4}$ to $10^{-6}$ cm$^2$/V.sec;

(d) specific activity according to the biological evaluation using L cell: at least $0.5 \times 10^9$ units/mg-protein;

(e) activity according to the biological evaluation using transplanted Meth A sarcoma in (BALB/c × C57BL/6)F$_1$ mouse when administered intravenously at a dose corresponding to 0.1 to 1 micrograms protein per mouse: (+) or higher; and (f) purity compared to that of the substance as induced in the rabbit: $2.8 \times 10^6$— to $8.1 \times 10^6$-fold.

4. A process for purifying a proteinaceous physiologically active substance having antitumor activity which is induced by administering to a rabbit at least one substance having a capacity for stimulating the reticuloendothelial system selected from the group consisting of Gram-positive bacteria, protozoas, yeasts, or synthetic high molecular weight compounds, and then injecting endotoxin from a Gram-negative bacterium into the rabbit, which comprises:

(1) contacting a crude solution of said proteinaceous physiologically active substance with a basic anion exchanger using a buffer solution of pH 6.0 to 9.0 and a salt concentration of not more than 0.2M, to have said physiologically active substance adsorbed on the anion exchanger;

(2) eluting the adsorbed physiologically active substance from the anion exchanger with a buffer solution of a higher salt concentration;

(3) subjecting the eluate containing said physiologically active substance to gel filtration with a gel suitable for separation of a substance with a molecular weight in the range of 30,000 to 70,000 and an eluent comprising a buffer solution of pH 6.0 to 9.0;

(4) subjecting the physiologically active eluate from step (3) to affinity chromatography on immobilized cibacron blue;

(5) subjecting the physiologically active eluate from step (4) to gel filtration as in step (3) above;

(6) subjecting the physiologically active eluate from step (5) to affinity chromatography using immobilized concanavalin A;

(7) subjecting the physiologically active eluate from step (6) above to polyacrylamide slab-electrophoresis; and, (8) subjecting the physiologically active eluate from step (7) to gel filtration as in step (3).

5. The process according to claim 4, wherein the salt concentration of the eluent on gel filtration in step (3) is 0.15–2.0M.

6. A purified proteinaceous physiologically active substance having antitumor activity which is produced by the process of claim 4, said substance having the following characteristic properties:
   (a) molecular weight by gel filtration and PAGE: $39,000 \pm 5,000$;
   (b) isoelectric point: pH $3.9 \pm 0.3$;
   (c) mobility in cellulose acetate electrophoresis (pH 8.6): $10^{-4}$ to $10^{-6}$ cm$^2$/V.sec;
   (d) specific activity according to the biological evaluation using L cell: at least $0.5 \times 10^9$ units/mg-protein;
   (e) activity according to the biological evaluation using transplanted Meth A sarcoma in (BALB/c × C57BL/6)F$_1$ mouse when administered intravenously at a dose corresponding to 0.1 to 1 micrograms protein per mouse: (+) or higher; and
   (f) purity compared to that of the substance as induced in the rabbit: $2.8 \times 10^6$– to $8.1 \times 10^6$-fold.

7. A process of claims 1 or 4, wherein the Gram-positive bacteria, protozoas, yeasts, or high molecular weight compounds are selected from the group consisting of *corynebacterium parvum, corynebacterium granulosum, mycobacterium smegmatis,* mycobacterium cal-mette-Guerin, *Nocardia erythropolis, Nocardia gardneri,* Plasmodium, Toxoplasma, Zymosan, pyran copolymer, and mixtures thereof.

8. A substance of claims 3 or 6, wherein the Gram-positive bacteria, protozoas, yeasts, or high molecular weight compounds are selected from the group consisting of *corynebacterium parvum, corynebacterium granulosum, mycobacterium smegmatis,* mycobacterium cal-mette-Guerin, *Nocardia erythropolis, Nocardia gardneri,* Plasmodium, Toxoplasma, Zymosan, pyran copolymer, and mixtures thereof.

9. A process of claims 1 or 4, wherein the endotoxin derived from a Gram-negative bacterium is a lipopolysaccharide derived from *Escherichia coli, Pseudomonas aeruginosa,* or *Salmonella typhosa.*

10. A substance of claims 3 or 6, wherein the endotoxin derived from a Gram-negative bacterium is a lipopolysaccharide derived from *Escherichia coli, Pseudomonas aeruginosa,* or *Salmonella typhosa.*

11. A process of claims 1 or 4, wherein the proteinaceous physiologically active substance has antitumor activity against human cancer cells.

12. A substance of claims 3 or 6, wherein the proteinaceous physiologically active substance has antitumor activity against human cancer cells.

* * * * *

UNITED STATES PATENT AND TRADEMARK OFFICE
CERTIFICATE OF CORRECTION

PATENT NO. : 5,023,320

DATED : June 11, 1991

INVENTOR(S) : Katsuyuki Haranaka et al.

It is certified that error appears in the above-identified patent and that said Letters Patent is hereby corrected as shown below:

On the title page of the patent, after "[22] Filed Jul. 14, 1988" add the following:

--[30] Foreign Application Priority Data

Dec. 28, 1981 [JP] Japan ............ 56-209840
    Dec. 28, 1981 [JP] Japan ............ 56-209841--.

In column 7, line 22, after "the column", insert --thoroughly--.

Signed and Sealed this

Third Day of November, 1992

Attest:

DOUGLAS B. COMER

*Attesting Officer*     *Acting Commissioner of Patents and Trademarks*